US010019794B2

(12) United States Patent
Jeong et al.

(10) Patent No.: US 10,019,794 B2
(45) Date of Patent: Jul. 10, 2018

(54) METHOD AND APPARATUS FOR BREAST LESION DIAGNOSIS

(71) Applicant: ELECTRONICS AND TELECOMMUNICATIONS RESEARCH INSTITUTE, Daejeon (KR)

(72) Inventors: Ji Wook Jeong, Daejeon (KR); Seung Hoon Chae, Damyang-gun (KR); Soo Yeul Lee, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 115 days.

(21) Appl. No.: 15/085,906

(22) Filed: Mar. 30, 2016

(65) Prior Publication Data
US 2016/0292852 A1 Oct. 6, 2016

(30) Foreign Application Priority Data
Mar. 31, 2015 (KR) .................. 10-2015-0045367

(51) Int. Cl.
G06T 7/00 (2017.01)
G06T 11/60 (2006.01)
A61B 6/00 (2006.01)
A61B 6/02 (2006.01)

(52) U.S. Cl.
CPC ............ G06T 7/0012 (2013.01); A61B 6/025 (2013.01); A61B 6/502 (2013.01); A61B 6/5217 (2013.01); G06T 11/60 (2013.01); G06T 2207/10072 (2013.01); G06T 2207/10112 (2013.01); G06T 2207/20221 (2013.01); G06T 2207/30068 (2013.01); G06T 2207/30096 (2013.01)

(58) Field of Classification Search
CPC .................. G06T 7/0012; G06T 11/60; G06T 2207/10072; G06T 2207/20221; G06T 2207/30068; G06T 2207/30096; G06T 2207/10112; A61B 6/025; A61B 6/502; A61B 6/5217; A61B 6/02
See application file for complete search history.

(56) References Cited

U.S. PATENT DOCUMENTS

| 7,615,008 B2 | 11/2009 | Zhang et al. |
| 2010/0260316 A1* | 10/2010 | Stein ............ A61B 6/025 378/37 |
| 2012/0014504 A1 | 1/2012 | Jang et al. |
| 2012/0210272 A1 | 8/2012 | Roehrig et al. |

(Continued)

FOREIGN PATENT DOCUMENTS

| KR | 10-0719350 B1 | 5/2007 |
| KR | 10-2012-0010585 A | 2/2012 |
| KR | 10-2014-0057130 A | 5/2014 |

Primary Examiner — Jon Chang

(57) ABSTRACT

Provided herein is an image interpretation auxiliary method for breast lesion diagnosis, the method including obtaining, by an image interpretation auxiliary apparatus, a plurality of 3D images photographed from a breast; determining, by the image interpretation auxiliary apparatus, a first image of among the plurality of 3D images as a basic image; and creating an image for interpretation, by the image interpretation auxiliary apparatus, by combining information related to a second image of among the plurality of 3D images with the first image.

19 Claims, 6 Drawing Sheets

(56) References Cited

U.S. PATENT DOCUMENTS

| | | | |
|---|---|---|---|
| 2012/0256920 A1* | 10/2012 | Marshall | A61B 6/025 345/420 |
| 2013/0116551 A1 | 5/2013 | Florent et al. | |
| 2013/0279777 A1* | 10/2013 | Serlie | G06T 7/0012 382/128 |
| 2014/0033126 A1* | 1/2014 | Kreeger | G06F 19/321 715/821 |
| 2014/0316260 A1 | 10/2014 | Jeon et al. | |
| 2016/0235380 A1* | 8/2016 | Smith | A61B 6/025 |

* cited by examiner

3D CONTOUR LINE MAP

METHOD AND APPARATUS FOR BREAST LESION DIAGNOSIS

CROSS-REFERENCE TO RELATED APPLICATION

The present application claims priority to Korean patent application number 10-2015-0045367, filed on Mar. 31, 2015, the entire disclosure of which is incorporated herein in its entirety by reference.

BACKGROUND

Field of Invention

Various embodiments of the present disclosure relate to an image interpretation auxiliary method and apparatus for breast lesion diagnosis, and more particularly, to an image interpretation auxiliary method and apparatus capable of combining a plurality of 'independent' '3-dimensional (3D) images' photographed from a breast so as to create an image for interpretation, thereby improving the accuracy of interpretation of a breast lesion.

Description of Related Art

Breast cancer is the most commonly diagnosed women cancer worldwide. It is a well-known fact that there are particularly a large number of young breast cancer patients in Korea just in their 40s. Breast ultrasonography and MR mammography are sometimes used for precision diagnosis, but it is the x-ray digital mammography that is generally used in regular examinations for breast cancer. Tumors have a 95% possibility of developing into breast cancer, and the x-ray digital mammography technique shows excellent performance in detecting micro-calcification, but its detectability for tumors is less than 80%, which is significantly lower than the tumor detectability of breast ultrasonography or MR mammography. Furthermore, due to the characteristics of 2-dimensional images, breast tissues may appear to be overlapping on a plane, making it difficult for doctors to interpret tumors, and thus the accuracy of detecting a tumor is not more than 50%, which is a problem.

A world-renowned x-ray image equipment company, Hologic, developed the DBT (Digital Breast Tomosynthesis) equipment, selenia dimensions, which doesn't have the problem of breast tissues appearing to be overlapping. This has received approval by FDA and is currently on the market, and has firmly established its stance as an advanced model of x-ray mammography.

With the development of image equipment for breast cancer inspection, techniques that could help image interpretation of those image equipment are also being developed.

For example, techniques for displaying image data of a breast together with results obtained from analyzing the image data, techniques for extracting image data of only the breast area by removing the background from the image data photographed from the breast, and techniques for processing image data of a breast to display only the cross-section of a certain slice area are being developed.

However, conventional image interpretation techniques focus on reprocessing a single image data. Therefore, in the case of interpreting a plurality of image data each created independently by different equipment, the plurality of image data need to be interpreted individually, making it difficult to interpret the data while comparing the exact corresponding positions between each image data.

Furthermore, conventional image interpretation techniques provide image analysis results using 2D models, and are therefore incapable of supporting intuitive image interpretation.

Therefore, there is a need to develop a new technique that could resolve these problems.

The present disclosure was invented based on the aforementioned technical background, and also to not only satisfy the aforementioned technical needs but also to provide additional technical elements that could not have been easily invented by one skilled in the art.

SUMMARY

Various embodiments of the present disclosure are directed to provide an image interpretation auxiliary technique capable of combining a plurality of '3-dimensional images (or information related to 3-dimensional images)' each 'independently' photographed from a breast so as to create an image for interpretation, thereby improving the accuracy of 'breast lesion interpretation'.

The aforementioned task of the present disclosure is not limited to the aforementioned, but may rather include various technical tasks within the scope apparent to one skilled in the art based on the description of the present disclosure that will be provided hereinafter.

According to an embodiment of the present disclosure, there is provided an image interpretation auxiliary method including obtaining, by an image interpretation auxiliary apparatus, a plurality of 3D images photographed from a breast; determining, by the image interpretation auxiliary apparatus, a first image of among the plurality of 3D images as a basic image; and creating an image for interpretation, by the image interpretation auxiliary apparatus, by combining information related to a second image of among the plurality of 3D images with the first image.

Furthermore, the creating an image for interpretation may involve overlaying the second image on the first image, to create the image for interpretation.

Furthermore, the image for interpretation may include an area of the first image emphasized by the second image.

Furthermore, the creating an image for interpretation may involve creating, by the image interpretation auxiliary apparatus, 2D image data based on the second image, and overlaying the created 2D image data on the first image, to create the image for interpretation.

Furthermore, the 2D image data may be image data created in an MIP (Maximum Intensity Projection) method, image data created through segmentation, or image data created in consideration of information on depth from skin.

Furthermore, the creating an image for interpretation may involve combining only a portion and not an entirety of the second image with the first image, to create the image for interpretation.

Furthermore, the portion of the second image being combined with the first image may be either an area selected by a user, or an area showing a possibility of existence of a breast lesion according to a result of processing the area.

Furthermore, the image interpretation auxiliary apparatus may combine an area of the first area corresponding to the portion of the area of the second image with the entirety of the second image, to create an additional image for interpretation.

Furthermore, the creating an image for interpretation may involve displaying CAD (Computer Assisted Diagnosis)

analysis information on the first image or CAD analysis information on the second image together with the image for interpretation.

Furthermore, the CAD analysis information may include MC (Micro Calcification) information or tumor information analyzed based on image data.

Furthermore, the first image or second image may be a 3D DBT (Digital Breast Tomosynthesis) image or a 3D DOT (Diffuse Optical Tomography) image.

Furthermore, the creating an image for interpretation may involve providing 3D surface information according to different depths of the image for interpretation.

Furthermore, the creating an image for interpretation may involve creating a 3D contour line map based on the first image, and combining the information related to the second image with the 3D contour map.

Meanwhile, the image interpretation auxiliary method may be realized in a program format, and then be stored in a record medium readable by an electronic apparatus or be distributed through a wired/wireless communication network.

According to another embodiment of the present disclosure, there is provided an image interpretation auxiliary apparatus including a 3D image managing unit configured to obtain a plurality of 3D images photographed from a breast; and an interpretation image creation unit configured to determine a first image of among the plurality of 3D images as a basic image, and to combine information related to a second image of among the plurality of 3D images with the first image, to create an image for interpretation.

Furthermore, the interpretation image creation unit may overlay the second image on the first image, to create the image for interpretation.

Furthermore, the interpretation image creation unit may create 2D image data based on the second image, and overlay the created 2D image data on the first image, to create the image for interpretation.

Furthermore, the interpretation image creation unit may combine only a portion and not an entirety of the second image with the first image, to create the image for interpretation.

Furthermore, the interpretation image creation unit may display CAD (Computer Assisted Diagnosis) analysis information on the first image or CAD analysis information on the second image together with the image for interpretation.

Furthermore, the first image or second image may be a 3D DBT (Digital Breast Tomosynthesis) image or a 3D DOT (Diffuse Optical Tomography) image.

The present disclosure is capable of combining a plurality of 3-dimensional image data (or information related to 3-dimensional images) photographed from a breast so as to create an image for interpretation, and may therefore improve the accuracy of breast lesion diagnosis. More specifically, the present disclosure is capable of combining a plurality of 3-dimensional data (or information related to 3-dimensional images) taken by different equipment so as to create an image for interpretation, and may therefore 'simultaneously' provide 'information obtained from a plurality of image equipment' regarding 'a certain area of a breast', thereby improving the accuracy of breast lesion diagnosis.

Furthermore, the present disclosure is capable of determining a certain image data of among a plurality of 3-dimensional image data as a basic image (reference image), and combining the plurality of image data based on the determined basic image, thereby improving the accuracy of image combination.

Furthermore, the present disclosure is capable of combining a plurality of 3-dimensional image data each created independently, so as to create a 3-dimensional image for interpretation, thereby improving intuitiveness of image interpretation.

Furthermore, the present disclosure is capable of combining a plurality of 3-dimensional image data with CAD (Computer Assisted Diagnosis) data regarding the plurality of 3-dimensional image data, so as to create an image for interpretation, and may therefore further improve the accuracy and intuitiveness of breast lesion diagnosis. More specifically, the present disclosure is capable of providing 'image data photographed by a plurality of equipment' and 'CAD information data that is an analysis of the image data photographed by the plurality of equipment' in an integrated manner through a single image for interpretation, and may therefore further improve the accuracy and intuitiveness of breast lesion diagnosis.

The aforementioned effects of the present disclosure are not limited to the aforementioned effects, but may include various effects within the scope apparent to one skilled in the art based on the description of the present disclosure that will be provided hereinafter.

BRIEF DESCRIPTION OF THE DRAWINGS

The above and other features and advantages of the present disclosure will become more apparent to those of ordinary skill in the art by describing in detail embodiments with reference to the attached drawings in which.

DETAILED DESCRIPTION

Figure 1:
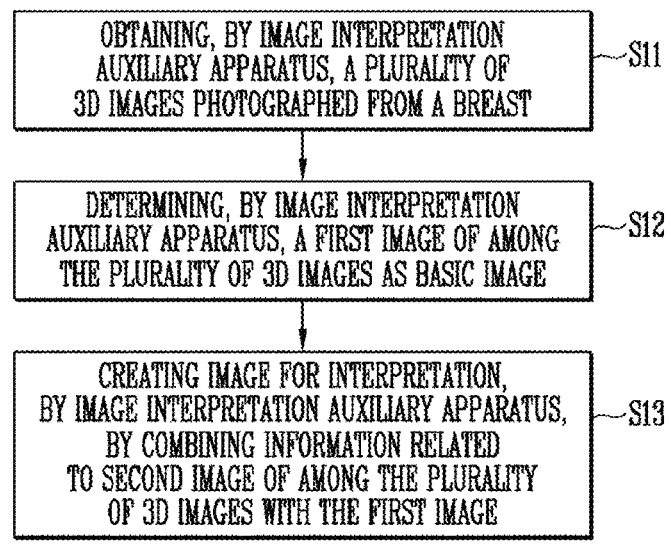
FIG. 1 is a flowchart of an image interpretation auxiliary method according to an embodiment of the present disclosure.

Hereinafter, embodiments will be described in greater detail with reference to the accompanying drawings. Embodiments are described herein with reference to cross-sectional illustrates that are schematic illustrations of embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but may include deviations in shapes that result, for example, from manufacturing. In the drawings, lengths and sizes of layers and regions may be exaggerated for clarity. Like reference numerals in the drawings denote like elements.

Terms such as 'first' and 'second' may be used to describe various components, but they should not limit the various components. Those terms are only used for the purpose of differentiating a component from other components. For example, a first component may be referred to as a second component, and a second component may be referred to as a first component and so forth without departing from the spirit and scope of the present invention. Furthermore, 'and/or' may include any one of or a combination of the components mentioned.

Furthermore, 'connected/accessed' represents that one component is directly connected or accessed to another component or indirectly connected or accessed through another component.

In this specification, a singular form may include a plural form as long as it is not specifically mentioned in a sentence. Furthermore, 'include/comprise' or 'including/comprising' used in the specification represents that one or more components, steps, operations, and elements exist or are added.

Furthermore, unless defined otherwise, all the terms used in this specification including technical and scientific terms have the same meanings as would be generally understood by those skilled in the related art. The terms defined in generally used dictionaries should be construed as having the same meanings as would be construed in the context of the related art, and unless clearly defined otherwise in this specification, should not be construed as having idealistic or overly formal meanings.

Hereinafter, an image interpretation auxiliary method according to an embodiment of the present disclosure will be explained with reference to FIGS. 1 to 7.

Referring to FIG. 1, an image interpretation auxiliary method according to an embodiment of the present disclosure may include obtaining, by an image interpretation auxiliary apparatus, a plurality of 3-dimensional (3D) images photographed from a breast (S11); determining, by the image interpretation auxiliary apparatus, a first image of among the plurality of 3-dimensional (3D) images as a basic image (S12); and creating, by the image interpretation auxiliary apparatus, an image for interpretation by combining information related to a second image of among the plurality of 3-dimensional images with the first image (S13).

Herein, the image interpretation auxiliary apparatus may be realized as one of various types of electronic apparatuses capable of processing data and displaying visual information.

Furthermore, the image interpretation auxiliary apparatus may be realized as a single electronic apparatus that includes hardware and software, or as a system where two or more electronic apparatuses operate in an interlocked manner to each other.

Furthermore, the image interpretation auxiliary method may be realized to include two or more electronic apparatuses (for example, a 'server apparatus' for processing main data, and 'display apparatus' for receiving and displaying the processed data) connected to one another through a wired or wireless network, or one of other various types of electrode apparatuses or system structures.

The step of S11 is where the image interpretation auxiliary apparatus obtains a plurality of 3-dimensional (3D) images photographed from a breast.

Herein, it is desirable that each of the plurality of 3D images is created independently from one another. For example, the plurality of 3D images may be 3D images created by different image obtaining methods (for example, CT, MRI, ultrasound wave and the like), or 3D images created by different image equipment (for example, DBT (Digital Breast Tomosynthesis) image equipment, DOT (Diffuse Optical Tomography) image equipment and the like).

The step of S12 is where the image interpretation auxiliary apparatus determines a first image of among the plurality of 3D images as a basic image.

In the case of creating a new image based on a plurality of 3D images, when the plurality of 3D images are simply combined (C=A*B) in voxel units or combined on equal terms, an image that is not familiar to the user or that is rather shoddy may be created. Furthermore, since the purpose of combining a plurality of 3D images is not to see an image of all the areas of a breast combined, but to make a more detailed examination on a certain area (a portion where existence of a lesion is suspected), combining all the plurality of 3D images of all the areas is quite inefficient in terms of data processing.

Therefore, the image interpretation auxiliary apparatus divides the plurality of 3D images into a 'basic image' and 'additional images', and uses the 'basic image' to provide the basic image of the breast, but it is desirable that for important parts, the image interpretation auxiliary apparatus provides 'images of the basic image and additional images combined'. (Of course, in some embodiments, it is also possible to combine the basic image and additional images of all the areas of the breast).

The step of S12 is where the image interpretation auxiliary apparatus determines a 'first image' that may serve as the 'basic image' of among the plurality of 3D images, for the aforementioned operations.

Meanwhile, the image interpretation auxiliary apparatus may dynamically change the image serving as the basic image of among the plurality of 3D images. For example, in the case where the image interpretation auxiliary apparatus obtained 3D images of A, B, and C, the image interpretation auxiliary apparatus may determine A as the basic image and create an image for interpretation, and then change the basic image to B, and thereby changing the image for interpretation accordingly.

The step of S13 is where the image interpretation auxiliary apparatus combines information related to a second image of among the plurality of 3D images with the first image, and creates an image for interpretation.

Herein, the 'information related to the second image' may be the 'second image data itself (original 3D data photographed)', '3D image data newly obtained by processing the second image', or '2D image data of the second image converted from 3D image data'. Furthermore, the processing of the second image may be emphasizing object characteristics, emphasizing linear characteristics, improving SNR, or converting to transparent images and the like, and the 2D image data may be image data created by an MIP (Maximum Intensity Projection) method, image data created through segmentation, or image data created in consideration of information on depth from the skin and the like.

Furthermore, the 'information related to the second image' may be information on an entirety of a breast, or information on a certain portion of the breast, wherein the certain portion of the breast may be an area selected by the user, or an area found to have a possibility of including a breast lesion according to a result of processing/analyzing the area.

Furthermore, examples of the method for creating an image for interpretation include various image processing methods such as a method of overlaying information related to the second image on the first image, and a method of combining information related to the second image and the first image in voxel units, and the like.

Figure 2:
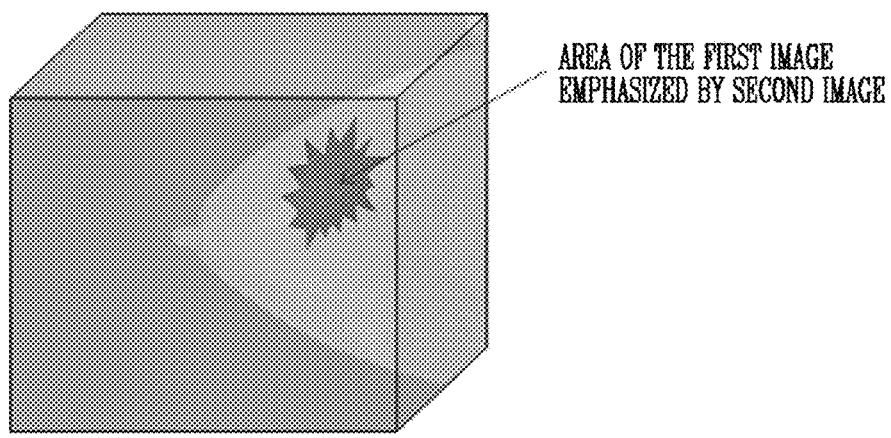
FIG. 2 is an exemplary view illustrating an exemplary format in which a plurality of 3-dimensional image data are combined.

FIG. 2 illustrates an exemplary format in which the 'information related to the second image' and the first image are combined.

As can be seen from FIG. 2, by being combined with the 'information related to the second image', the first image may be emphasized or compensated, and an image for interpretation will be created accordingly. Therefore, in the image for interpretation created accordingly, the problems of the first image will have been compensated using the second image, whereby the efficiency and accuracy of diagnosing a breast lesion may be improved. (For example, in the case where the first image is excellent in micro-calcification but poor in tumor detectability, the problems of the first image may be compensated by combining the first image with the second image showing excellence in tumor detectability).

Meanwhile, the image interpretation auxiliary apparatus is capable of dynamically changing the setting regarding the basic image, and of creating additional interpretation images according to such changes in the setting regarding the basic image. For example, the image interpretation auxiliary apparatus may set the second image as the basic image, and combine the second image with an entirety or a portion of the first image, so as to create an additional interpretation image that is based on the second image.

Furthermore, the image interpretation auxiliary apparatus may display CAD (Computer Assisted Diagnosis) analysis information on the first image and CAD analysis information on the second image together on the image for interpretation. Therefore, in such an embodiment, the image for interpretation may include all 'the first and second image combined', 'CAD analysis information on the first image', and 'CAD analysis information on the second image'.

Herein, the CAD analysis information may be created/added in connection with a certain 3D area (a certain breast area with a 3D volume), a certain 2D area (a certain breast area in a slice cross-sectional format), and a certain one-dimensional area (a certain point of the breast). Furthermore, the CAD analysis information may desirably include MC (Micro Calcification) information and tumor information that have been analyzed based on the image data.

Figure 3:
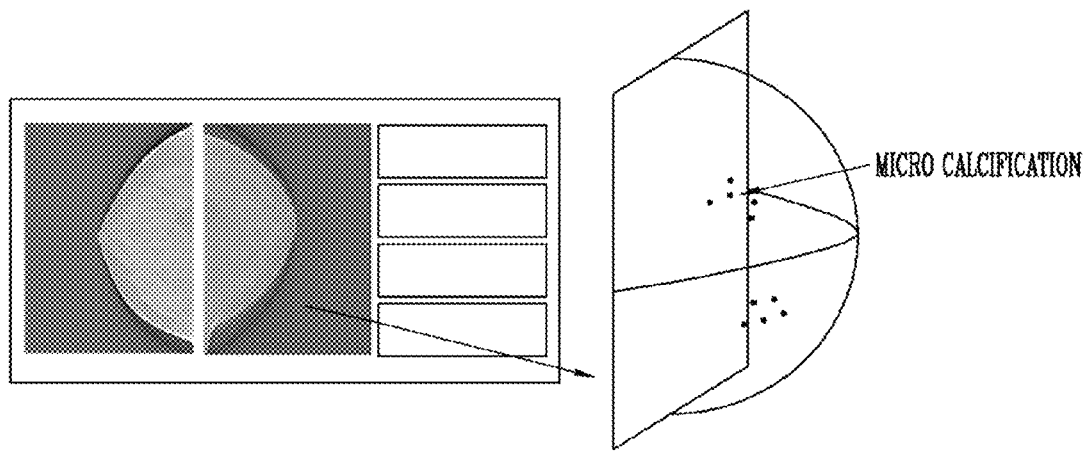
FIGS. 3 and 4 are exemplary views illustrating exemplary formats in which CAD information is added to an image for interpretation.
Figure 4:
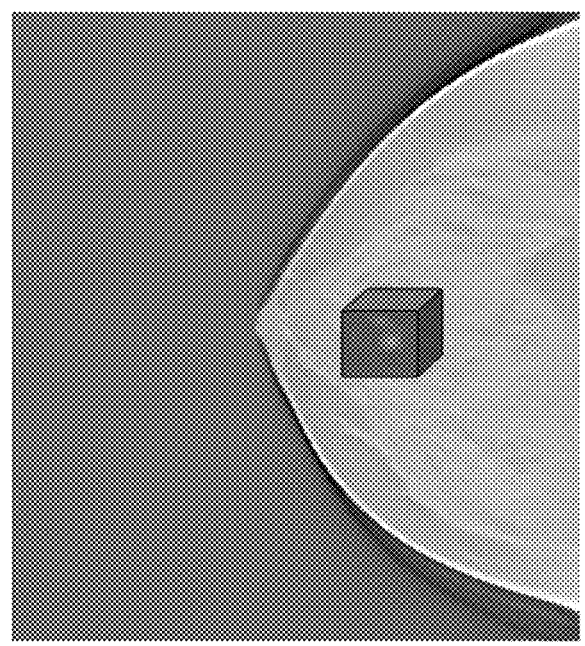

Furthermore, the CAD analysis information may be added to the image for interpretation in an object icon format (cube, or globular shape and the like) as illustrated in FIGS. 3 and 4, or the CAD analysis information may be configured in a format connected with a cartwheel video. Herein, the cartwheel video may desirably be based on a centroid of volume.

Furthermore, the image interpretation auxiliary apparatus may process the first image, and then perform a combination based on the processed image result to create the image for interpretation.

More specifically, the image interpretation auxiliary apparatus may create the image for interpretation using 1) the first image itself (3D original image itself), but instead, the image interpretation auxiliary apparatus may apply various image processing methods (for example, image processing for improving object characteristics, image processing for improving linear characteristics, image processing for improving SNR, and transparent image processing and the like) to the first image, and then create the image for interpretation using the processed first image.

Figure 5:
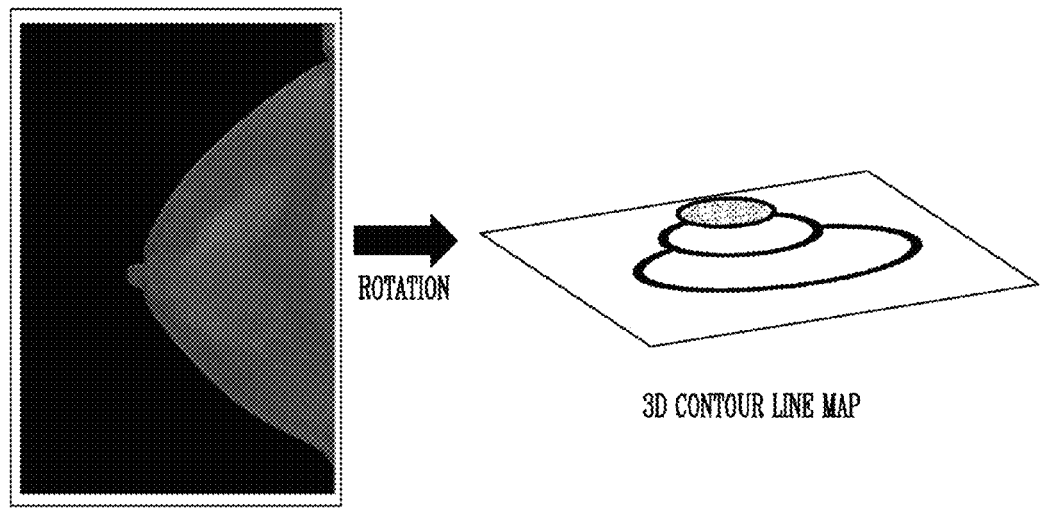
FIG. 5 is an exemplary view illustrating an exemplary 3-dimensional contour line being created from image data.

Furthermore, as illustrated in FIG. 5, the image interpretation auxiliary apparatus may create a 3D contour line map of the first image using the first image, or combine the 'information related to the second image' with the created 3D contour line map and create the image for interpretation. For example, the image interpretation auxiliary apparatus may analyze the first image and create a level set contour surface based on a certain criteria (for example, a constant brightness band), and create a 3D contour line map based on such a level set contour surface, and then create the image for interpretation.

Furthermore, the image interpretation auxiliary apparatus may create the image for interpretation, and then realize additional functions that could help the diagnosis process. For example, the image interpretation auxiliary apparatus may enable a function of setting an ROI (Region of Interest) of a certain point, a certain slice cross-sectional view, or a certain 3D volume area, or provide a cartwheel video of the set ROI (desirably, a cartwheel video that is based on a centroid of volume).

Figure 6:
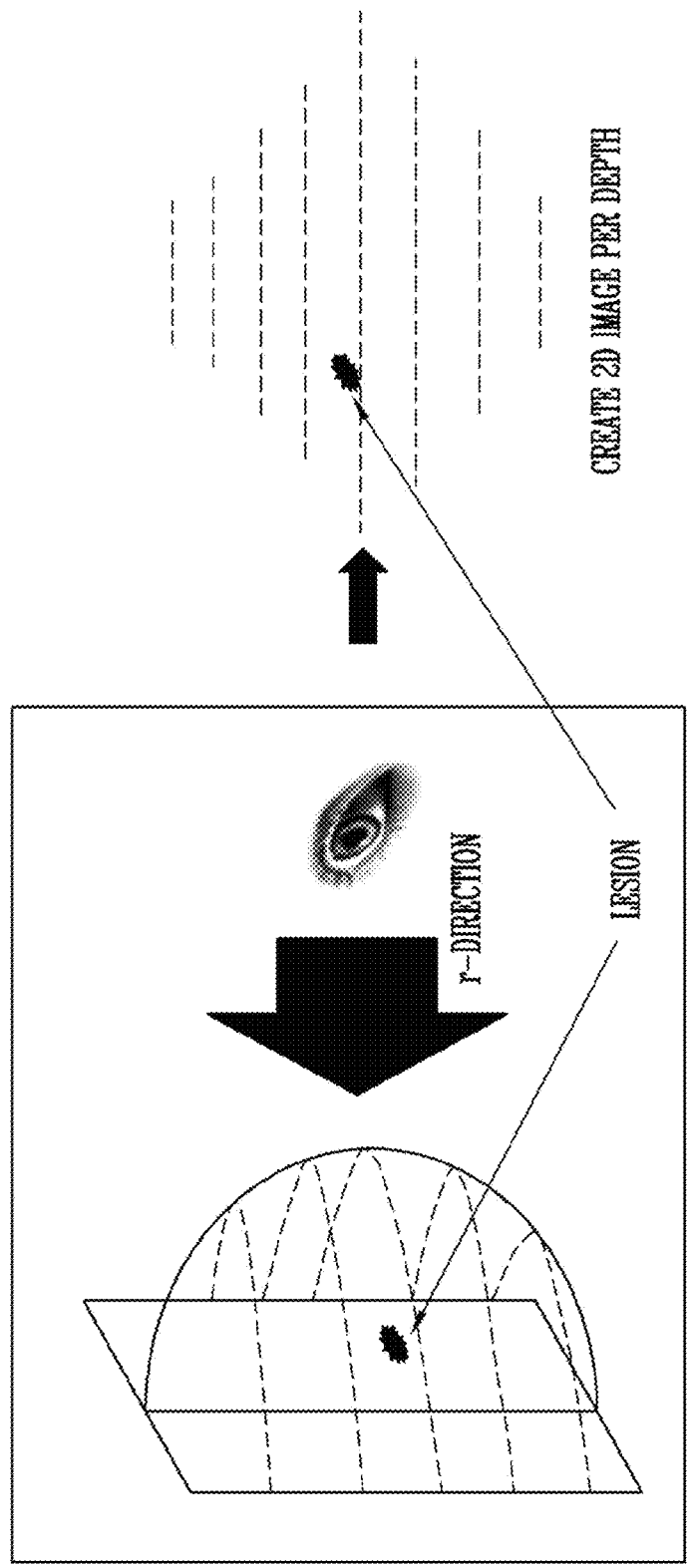
FIG. 6 is an exemplary view illustrating a method of providing additional information on an image for interpretation.

Furthermore, the image interpretation auxiliary apparatus may perform an operation of converting a 3D image volume included in the image for interpretation into another type of coordinate such as a cylindrical coordinate and spherical coordinate and the like. Furthermore, the image interpretation auxiliary apparatus may perform an operation of providing image data of which the image volume has been converted into a cylindrical coordinate or spherical coordinate on a contour surface having a constant r value in r axis direction, as illustrated in FIG. 6. Therefore, through these operations, the image interpretation auxiliary apparatus enables one to diagnose a breast lesion in various perspectives, thereby improving the accuracy of diagnosis.

FIG. 6 is an exemplary view illustrating a method of providing additional information on an image for interpretation.

Figure 7:
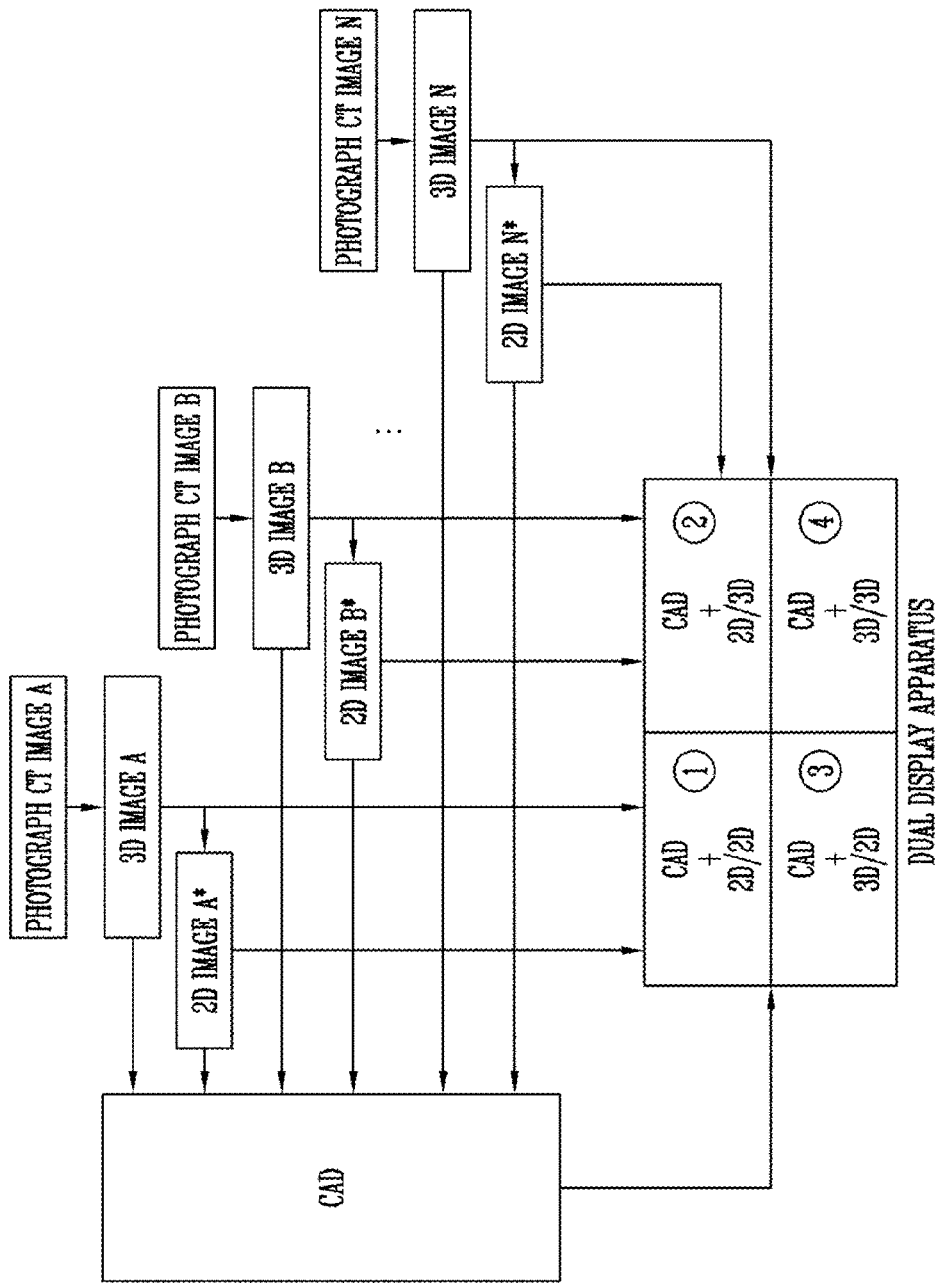
FIG. 7 is a block diagram illustrating an exemplary process of creating various types of images for interpretation.

FIG. 7 illustrates an exemplary process that may be performed by the image interpretation auxiliary apparatus in relation to creating an image for interpretation.

As can be seen from FIG. 7, the image interpretation auxiliary apparatus may obtain a plurality of 3D images (image A, image B, . . . image N) created independently from one another, and process the obtained plurality of 3D images to create 2D images (image A*, image B*, . . . image N*) of the 3D images, respectively. Furthermore, the image interpretation auxiliary apparatus may create CAD analysis information on the plurality of 3D images (image A, image B, . . . image N) and the plurality of 2D images (image A*, image B*, . . . image N*).

Thereafter, the image interpretation auxiliary apparatus may set one of the plurality of 3D images (image A, image B, . . . image N) as a basic image (for example, image A), and set the rest of the images (image B, . . . image N) as additional images.

Thereafter, the image interpretation auxiliary apparatus may combine the images with the CAD information on the images to create an image for interpretation. For example, the image interpretation apparatus may combine the rest of the 2D images (image B*, . . . image N*) to the 3D image A, and combine the CAD analysis information on the images thereto, to create an image for interpretation (case ① in FIG. 7). Furthermore, the image interpretation auxiliary apparatus may combine the rest of the 3D images (image B, . . . image N) to the 3D image A, and combine the CAD analysis information on the images thereto, to create an image for interpretation (case ② in FIG. 7). Meanwhile, the plurality of 3D images being used in creating the image for interpretation may be original data itself or image data that has been processed.

Meanwhile, the image interpretation auxiliary apparatus may additionally create an image for interpretation using a 2D basic image.

More specifically, the image interpretation auxiliary apparatus may set one of a plurality of 2D images created from the plurality of 3D images as a basic image (for example, image A*), and create an image for interpretation based on the set 2D basic image. For example, the image interpretation auxiliary apparatus may combine the rest of the 2D images (image B*, . . . image N*) to the 2D image A*, and combine the CAD analysis information on the images thereto, to create an image for interpretation (case ③ in FIG. 7). Furthermore, the image interpretation auxiliary apparatus may combine the rest of the 3D images (image A, image B, . . . image N) to the 2D image A*, and combine the CAD analysis information on the images thereto, to create an image for interpretation (case ④ in FIG. 7).

Meanwhile, the image interpretation auxiliary method may be realized in a program format, and then be stored in a record medium readable by an electronic apparatus, or be distributed in a format downloadable in various types of electronic apparatuses through a wired/wireless communication network.

Hereinafter, an image interpretation auxiliary apparatus according to an embodiment of the present disclosure will be explained with reference to FIGS. 8 to 9.

The image interpretation auxiliary apparatus according to the embodiment of the present disclosure that will be explained hereinafter may include substantially the same (or corresponding) technical characteristics as the image interpretation auxiliary method of an embodiment of the present disclosure mentioned hereinabove, but just having a different category. Therefore, the various technical characteristics mentioned above with relation to the image interpretation auxiliary method may also be applied to the image interpretation auxiliary apparatus even though detailed explanation is omitted to avoid repetition of explanation.

Figure 8:
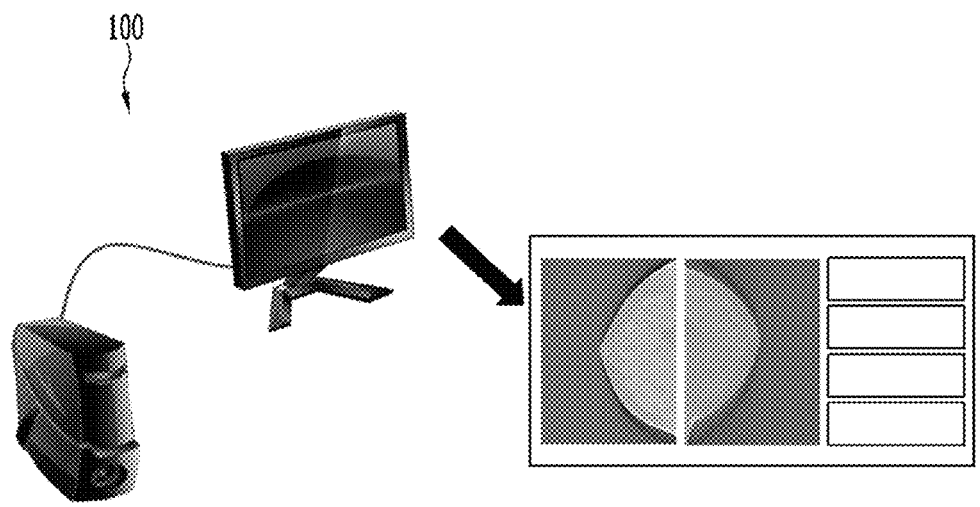
FIG. 8 is an exemplary view illustrating an exemplary format of an image interpretation auxiliary apparatus.
Figure 9:
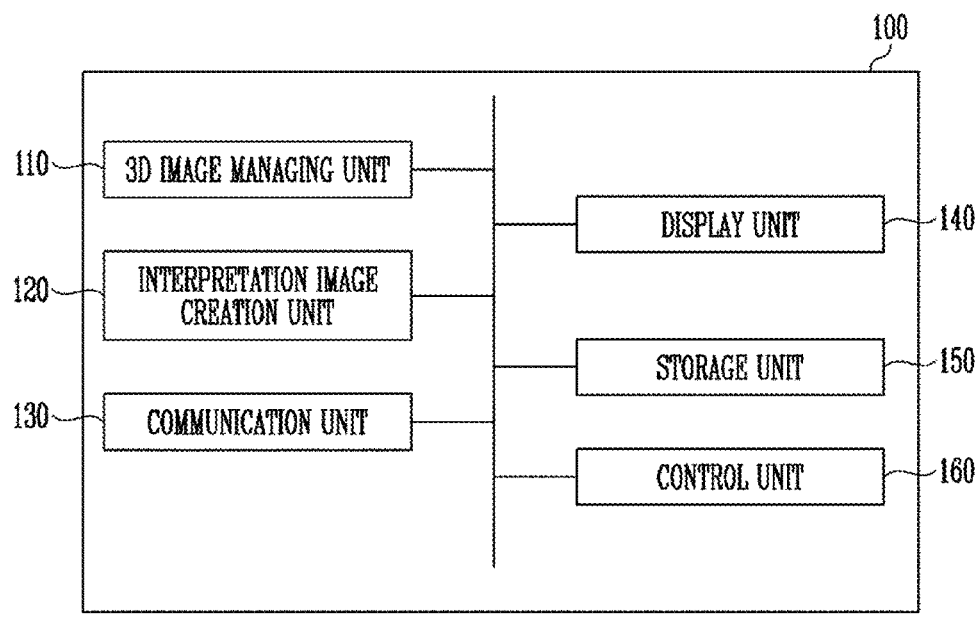
FIG. 9 is a configuration diagram illustrating exemplary configurations of an image interpretation auxiliary apparatus according to an embodiment of the present disclosure.

Referring to FIGS. 8 to 9, the image interpretation auxiliary apparatus according to an embodiment of the present disclosure 100 may include a 3D image managing unit 110, interpretation image creation unit 120, communication unit 130, display unit 140, storage unit 150, and control unit 160. The image interpretation auxiliary apparatus may also include other components besides these.

Meanwhile, each of these components may be realized by hardware only or by software only, or in a combination of hardware and software. Furthermore, two or more components may be realized by one hardware or software.

The 3D image managing unit 110 is configured to obtain and manage a plurality of 3D images photographed from a breast.

Such a 3D image managing unit 110 may obtain a plurality of 3D images. More specifically, the 3D image managing unit 110 may obtain various types of 3D images including for example, DBT (Digital Breast Tomosynthesis) images and DOT (Diffuse Optical Tomography) image, and the like.

Furthermore, the 3D image managing unit 110 may perform other various operations mentioned earlier on in relation to obtaining or managing image data.

The interpretation image creation unit 120 is configured to determine a first image of among the plurality of 3D images as a basic image, and to combine information related to a second image of among the plurality of 3D images with the first image, to create an image for interpretation.

Herein, the first image or second image may be a 3D DBT (Digital Breast Tomosynthesis) image or a 3D DOT (Diffuse Optical Tomography) image.

Furthermore, the interpretation image creation unit 120 may overlay the second image on the first image, to create an image for interpretation.

Furthermore, the interpretation image creation unit 120 may create 2D image data based on the second image, and overlay the created 2D image data on the first image, to create an image for interpretation.

Furthermore, the interpretation image creation unit 120 may combine only a portion of the second image and not an entirety of the second image with the first image, to create an image for interpretation.

Furthermore, the interpretation image creation unit 120 may display CAD (Computer Assisted Diagnosis) analysis information on the first image or CAD analysis information on the second image together on the image for interpretation.

The interpretation image creation unit 120 may perform various operations other than those mentioned hereinabove with relation to creating an image for interpretation.

The communication unit 130 is configured to transmit/receive information to and from various electronic apparatuses including a plurality of medical image equipment through a wired or wireless communication network. Such a communication unit 130 may be realized to include various types of wired communication modules or wireless communication modules.

The display unit 140 is configured to display various pieces of information in visual formats. Such a display unit 140 may display the plurality of 3D images, image for interpretation, and analyzed CAD information and the like in visual formats, and also other various kinds of information mentioned hereinabove.

Furthermore, the display unit 160 may be realized through various types of display apparatuses.

The storage unit 150 is configured to store various types of information related to operations of the image interpretation auxiliary apparatus 100. For example, the storage unit 150 may store various types of information including for example, a plurality of 3D image data obtained from a plurality of image equipment, data result from processing the plurality of 3D image data or from converting 3D image data into 2D image data, data for image processing or image conversion, data for performing a CAD analysis, data result from CAD analysis conducted on each image data, and created image data for interpretation. Such a storage unit 150 may be realized to include various types of memory devices.

The control unit 160 is configured to control various operations of the image interpretation auxiliary apparatus 100 including the operations of the 3D image managing unit 110, interpretation image creation unit 120, communication unit 130, display unit 140, and storage unit 150.

Such a control unit 160 may include at least one processing unit. Herein, the processing unit may be a general CPU (Central Processing Unit), a programmable device realized to fit a certain purpose (for example, CPLD, FPGA), ASIC (Application-Specific Integrated Circuit), or a micro-controller chip.

In the drawings and specification, there have been disclosed typical exemplary embodiments of the invention, and although specific terms are employed, they are used in a generic and descriptive sense only and not for purposes of limitation. As for the scope of the invention, it is to be set forth in the following claims. Therefore, it will be understood by those of ordinary skill in the art that various changes in form and details may be made therein without departing from the spirit and scope of the present invention as defined by the following claims.

What is claimed is:

1. An image interpretation auxiliary method comprising:
    obtaining, by an image interpretation auxiliary apparatus, a plurality of 3D images of a breast;
    determining, by the image interpretation auxiliary apparatus, a first image among the plurality of 3D images as a basic image; and
    creating, by the image interpretation auxiliary apparatus, an image for interpretation by creating a 3D contour line map of the breast based on the first image, and combining a second image with the 3D contour line map, the second image corresponding to one of the plurality of 3D images.

2. The method according to claim 1,
    wherein combining the second image with the 3D contour line map includes:
    overlaying, by the image interpretation auxiliary apparatus, the second image on the 3D contour line map.

3. The method according to claim 2,
    wherein the image for interpretation comprises an area of the first image emphasized by the second image.

4. The method according to claim 1,
    wherein the creating an image for interpretation includes:
    creating, by the image interpretation auxiliary apparatus, the second image by generating 2D image data based on the 3D image corresponding to the second image.

5. The method according to claim 4,
    wherein the 2D image data is image data created by applying a Maximum Intensity Projection (MIP) method to the 3D image corresponding to the second image, by segmentation, or based on information on depth from skin.

6. The method according to claim 1,
    wherein the creating the image for interpretation includes:
    combining a first portion of the second image with the 3D contour line map, without combining a second portion of the second image with the 3D contour line map.

7. The method according to claim 6,
    wherein the first portion of the second image is an area selected by a user, or an area showing a possibility of existence of a breast lesion according to a result of processing the area.

8. The method according to claim 1, further comprising:
    creating an additional image for interpretation, by the image interpretation auxiliary apparatus, by combining a portion of the first image with the entirety of the second image.

9. The method according to claim 1,
    wherein the creating the image for interpretation includes:
    displaying Computer Assisted Diagnosis (CAD) analysis information on the image for interpretation.

10. The method according to claim 9,
    wherein the CAD analysis information comprises Micro Calcification (MC) information or tumor information analyzed based on image data.

11. The method according to claim 1,
    wherein the first image or the second image is a 3D Digital Breast Tomosynthesis (DBT) image or a 3D Diffuse Optical Tomography (DOT) image.

12. The method according to claim 1,
    wherein creating the image for interpretation includes:
    providing 3D surface information according to different depths of the image for interpretation.

13. A non-transitory recording medium readable by an electronic apparatus, wherein a program for realizing an image interpretation auxiliary method is stored, the method comprising:
    obtaining, by an image interpretation auxiliary apparatus, a plurality of 3D images of a breast;
    determining, by the image interpretation auxiliary apparatus, a first image among the plurality of 3D images as a basic image; and
    creating, by the image interpretation auxiliary apparatus, an image for interpretation by creating a 3D contour line map of the breast based on the first image, and combining a second image with the 3D contour line map, the second image corresponding to one of the plurality of 3D images.

14. An image interpretation auxiliary apparatus comprising:
    a 3D image managing unit configured to obtain a plurality of 3D images of a breast; and
    an interpretation image creation unit configured to determine a first image among the plurality of 3D images as a basic image, and to create an image for interpretation by combining information related to a second image with a 3D contour line map of the breast based on the first image, the second image being among the plurality of 3D images.

15. The apparatus according to claim 14,
    wherein the interpretation image creation unit creates the image for interpretation by overlaying the first portion of the second image on the first image.

16. The apparatus according to claim 14,
    wherein the interpretation image creation unit is further configured to generate the second image by creating 2D image data based on the 3D image corresponding to the second image, and
    wherein the interpretation image creation unit creates the image for interpretation by overlaying the created 2D image data on the 3D contour map.

17. The apparatus according to claim 14,
    wherein the interpretation image creation unit creates the image for interpretation by combining a first portion of the second image with the 3D contour map without combining a second portion of the second image with the 3D contour map.

18. The apparatus according to claim 14,
    wherein the interpretation image creation unit displays Computer Assisted Diagnosis (CAD) analysis information with the image for interpretation.

19. The apparatus according to claim 14,
    wherein the first image or the second image is a 3D Digital Breast Tomosynthesis (DBT) image or a 3D Diffuse Optical Tomography (DOT) image.

* * * * *